(12) United States Patent
Roell et al.

(10) Patent No.: US 8,788,016 B2
(45) Date of Patent: Jul. 22, 2014

(54) DEVICE FOR RADIATION THERAPY UNDER IMAGE MONITORING

(75) Inventors: Stefan Roell, West Chester, PA (US); Sebastian Schmidt, Weisendorf (DE); Anke Siebert, Forchhheim (DE)

(73) Assignee: Siemens Aktiengesellschaft, Munich (DE)

( * ) Notice: Subject to any disclaimer, the term of this patent is extended or adjusted under 35 U.S.C. 154(b) by 795 days.

(21) Appl. No.: 12/271,075

(22) Filed: Nov. 14, 2008

(65) Prior Publication Data

US 2009/0124887 A1 May 14, 2009

(30) Foreign Application Priority Data

Nov. 14, 2007 (DE) .......................... 10 2007 054 324

(51) Int. Cl.
*A61B 5/055* (2006.01)
(52) U.S. Cl.
USPC .......................................... 600/411; 600/415
(58) Field of Classification Search
USPC .......................................... 600/411, 407, 415
See application file for complete search history.

(56) References Cited

U.S. PATENT DOCUMENTS

| | | | |
|---|---|---|---|
| 5,153,546 A * | 10/1992 | Laskaris | 335/216 |
| 5,818,901 A | 10/1998 | Schulz | |
| 5,917,395 A | 6/1999 | Overweg | |
| 6,094,590 A * | 7/2000 | Kan et al. | 600/411 |
| 6,198,957 B1 * | 3/2001 | Green | 600/411 |
| 6,414,490 B1 * | 7/2002 | Damadian et al. | 324/319 |
| 6,487,274 B2 | 11/2002 | Bertsche | |
| 6,677,752 B1 * | 1/2004 | Creighton et al. | 324/318 |
| 6,725,078 B2 | 4/2004 | Bucholz et al. | |
| 6,828,792 B1 * | 12/2004 | Danby et al. | 324/318 |
| 6,862,469 B2 * | 3/2005 | Bucholz et al. | 600/411 |
| 7,123,008 B1 | 10/2006 | Damadian et al. | |
| 7,167,741 B2 * | 1/2007 | Torchia et al. | 600/427 |
| 7,404,674 B2 * | 7/2008 | Eichenseer | 378/209 |
| 2001/0049475 A1 * | 12/2001 | Bucholz et al. | 600/411 |
| 2002/0016544 A1 * | 2/2002 | Hareyama et al. | 600/411 |
| 2003/0131855 A1 * | 7/2003 | Carter et al. | 128/870 |
| 2004/0030241 A1 * | 2/2004 | Green et al. | 600/422 |
| 2004/0138553 A1 * | 7/2004 | Damadian | 600/410 |
| 2004/0199068 A1 * | 10/2004 | Bucholz et al. | 600/411 |
| 2005/0187459 A1 * | 8/2005 | Trequattrini et al. | 600/415 |
| 2005/0197564 A1 | 9/2005 | Dempsey | |
| 2005/0203399 A1 * | 9/2005 | Vaezy et al. | 600/439 |
| 2005/0248347 A1 * | 11/2005 | Damadian | 324/318 |
| 2007/0225619 A1 * | 9/2007 | Rabiner et al. | 601/2 |
| 2008/0208036 A1 * | 8/2008 | Amies et al. | 600/411 |

FOREIGN PATENT DOCUMENTS

WO   WO 99/53997   10/1999
WO   WO 03/008986   1/2003

* cited by examiner

*Primary Examiner* — Long V Le
*Assistant Examiner* — Michael Kellogg
(74) *Attorney, Agent, or Firm* — Schiff Hardin LLP

(57) ABSTRACT

A device for radiation therapy implemented with image monitoring has a magnetic resonance device and an exposure device. The magnetic resonance device has a magnet and primarily serves for image monitoring an examination object of a patient in an examination volume of the magnetic resonance device. The exposure is fashioned to be static and serves to expose the examination subject in the examination volume with therapeutic beams. The patient (and therefore the examination subject) are supported by a patient positioning device such that the examination subject can be moved relative to the magnetic resonance device and the exposure device around at least one rotation axis.

12 Claims, 3 Drawing Sheets

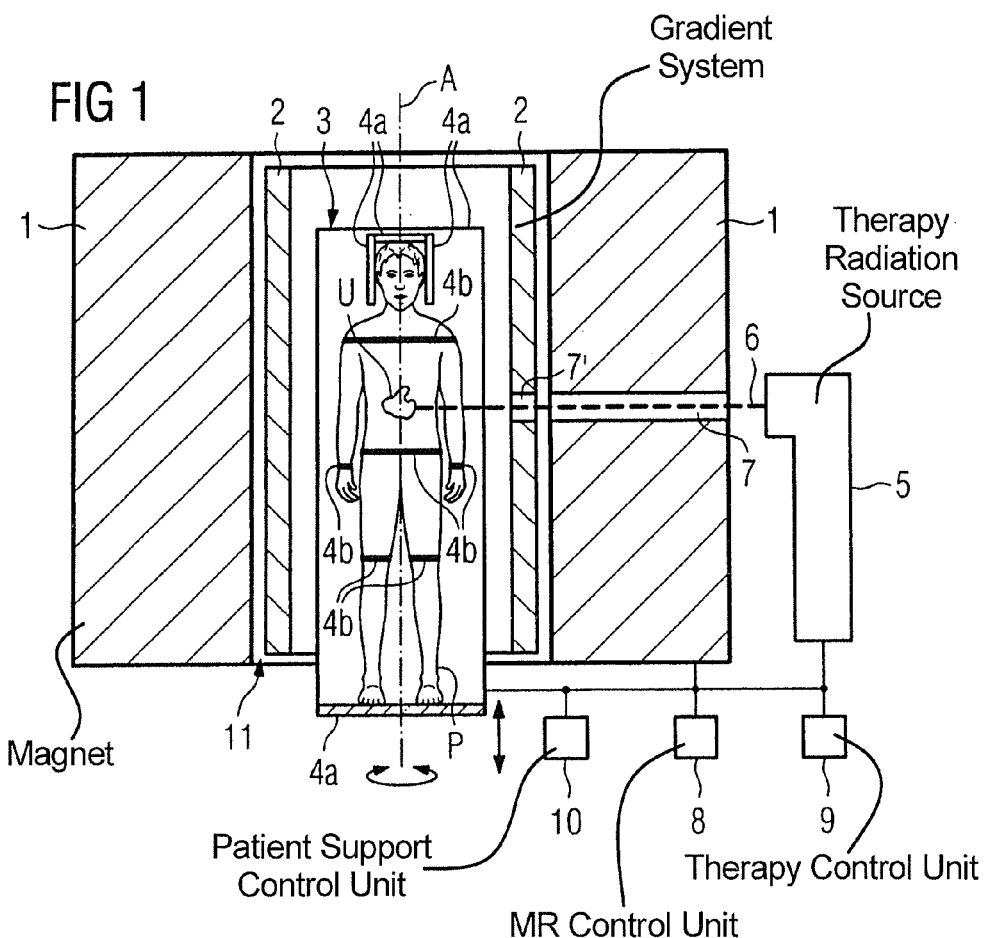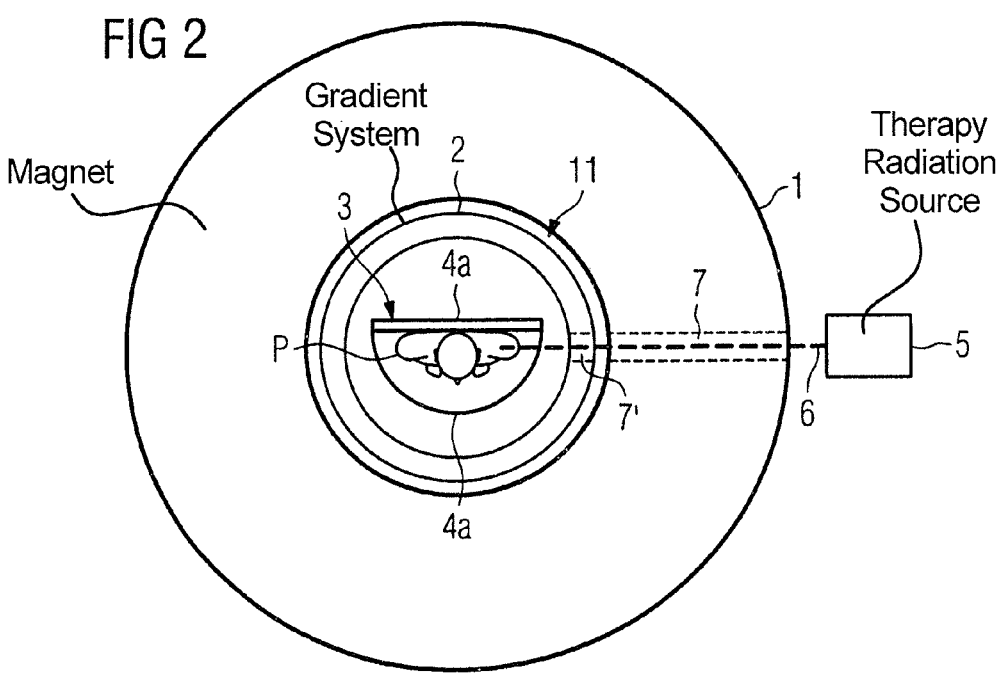

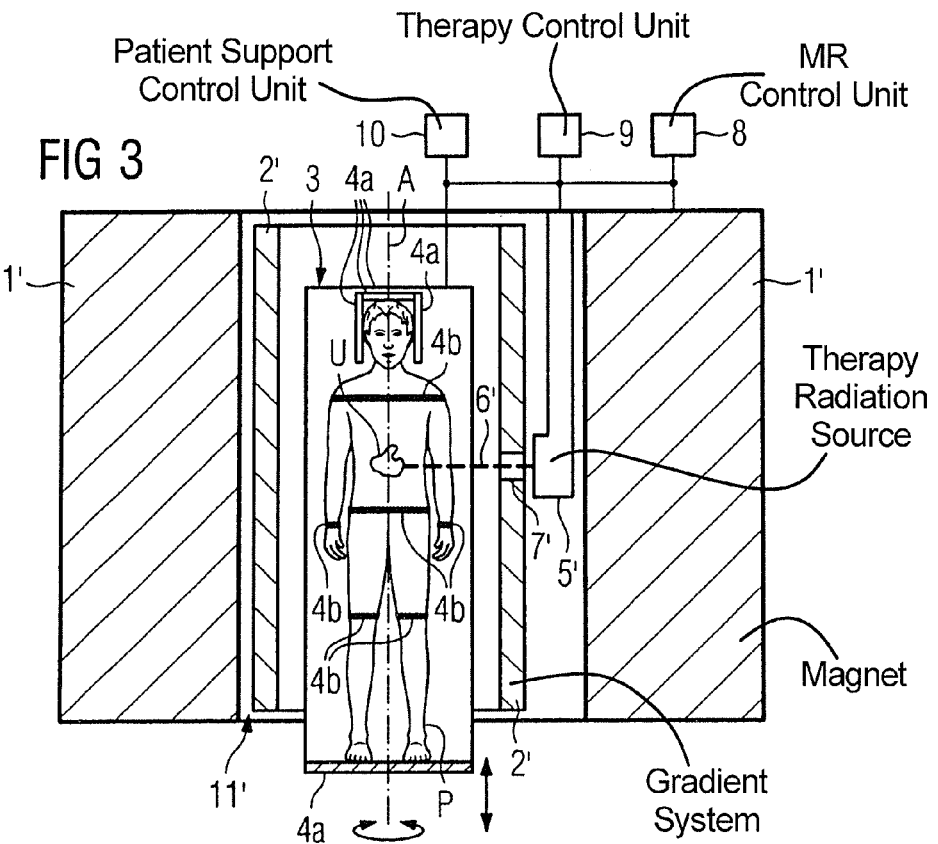
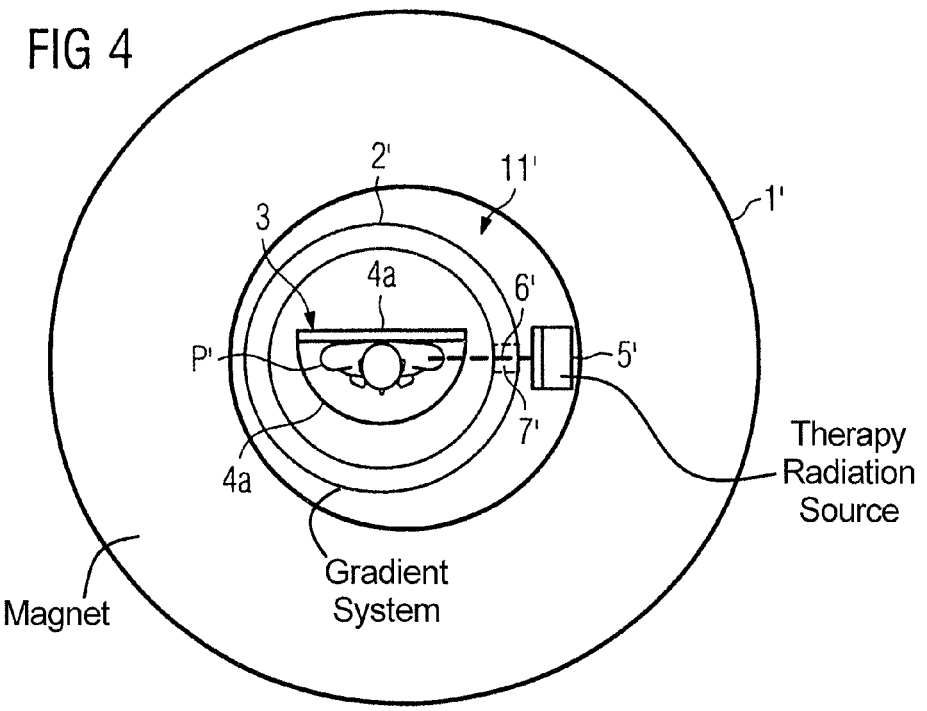

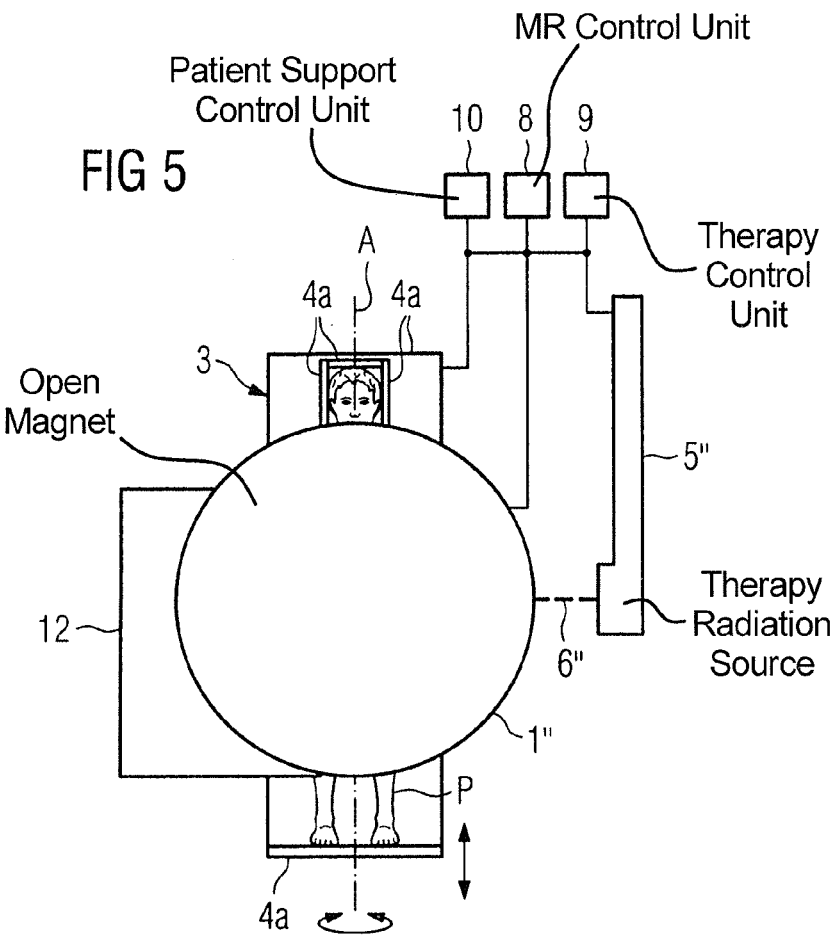

DEVICE FOR RADIATION THERAPY UNDER IMAGE MONITORING

BACKGROUND OF THE INVENTION

1. Field of the Invention

The present invention concerns a device for radiation therapy implemented with image monitoring.

2. Description of the Prior Art

In the framework of radiation therapy, in general a target within the human body should be irradiated in order to combat illnesses, in particular cancer. A high radiation dose is generated specifically in an exposure center (isocenter) of an exposure device. In order to minimize the radiation dose outside of the target volume and thus to protect healthy tissue, the entire radiation generator is normally moved around the static patient. The radiation dose is thereby concentrated in the beam in the region of the rotation axis.

However, in the exposure the problem frequently arises that the target of the exposure in the body is mobile. For example, a tumor in the abdominal region shifts during the breathing cycle. Moreover, a tumor can also shift, grow or already shrink in the time period between the exposure planning and the actual exposure. It is therefore known to monitor the position of the exposure target in the body during the exposure by imaging in order to be able to appropriately control the beam, or possibly to be able to terminate the exposure, and thus to increase the success of the therapy.

For this purpose, combinations of exposure devices with x-ray-based imaging have been proposed. These known combinations have the disadvantage that the image quality of x-ray-based imaging techniques is not optimal for the depiction of soft tissue (for example tumors), and that monitoring cannot occur simultaneously with the actual exposure (known as "in-line monitoring") due to interactions between x-rays of the imaging device and therapeutic beams of the exposure device. An example of such a combination is described in U.S. Pat. No. 6,487,274 B2.

Furthermore, combinations of exposure devices with MRI apparatuses (MRI: magnetic resonance imaging) have been proposed to enable an "in-line monitoring". Compared to combinations with x-ray-based imaging, such combinations offer the advantage that the imaging is less distorted by the exposure and a higher image quality is achieved.

For example, a radiation therapy apparatus with a system for magnetic resonance imaging (MRI system) in which a linear accelerator can be rotated around various axes is known in U.S. Pat. No. 6,198,957 B1. Depending on the selection of the rotation axes, however, parts of the MRI system also lie in the beam path of the radiation therapy apparatus and can thereby scatter and/or attenuate the beam.

United States Patent Application Publication No. 2005/0197564 A1 and WO 03/008986 A2 disclose respective systems for MRI-directed radiation therapy, wherein a radiation therapy unit is arranged between two parts of a bipartite magnet of an MRI apparatus so that the radiation therapy unit can be rotated around a center of the static, divided magnet. Such bipartite magnets are large, expensive and normally achieve a homogeneous magnetic field only in a small volume.

Therefore, a need continues to exist for devices for radiation therapy with image monitoring.

SUMMARY OF THE INVENTION

An object of the present invention is to provide exemplary embodiments of a device for radiation therapy under image monitoring that avoid the aforementioned disadvantages.

According to the invention, a device for radiation therapy under image monitoring has a magnetic resonance device and an exposure device. The magnetic resonance device has a magnet and serves primarily for image monitoring of an examination subject of a patient in an examination volume of the magnetic resonance device. The exposure device is fashioned to be static and serves for the exposure of the examination subject in the examination volume with therapeutic beams. The patient (and therefore the examination subject) are supported by a patient positioning device such that the examination subject can be moved relative to the magnetic resonance device and the exposure device around at least one rotation axis.

In particular, the static design of the exposure device allows a significant reduction of the volume required for said device. Moreover, a static exposure device is technically less complicated and therefore easier and cheaper to realize. At the same time, the quality of the exposure is thereby not negatively influenced by the possibility of a rotation of the examination subject, and an applied radiation dose outside of the target volume can furthermore be minimized, healthy tissue can thus be protected.

The patient support that carries the device for radiation therapy under image monitoring advantageously has fixing component to fix the patient to the support components. The fixing means prevent an unintentional movement of the patient and ensure that the patient need expend no force during the exposure in order to hold a specific position. Moreover, by preventing unintentional movement, the image monitoring is facilitated and thus the precision and quality of a target-specific exposure of the examination subject are promoted.

BRIEF DESCRIPTION OF THE DRAWINGS

FIG. 1 shows a first embodiment of a device for radiation therapy under image monitoring, schematically in a longitudinal section, in accordance with the invention.

FIG. 2 shows the first embodiment of a device for radiation therapy under image monitoring, schematically in plan view.

FIG. 3 shows a second embodiment of a device for radiation therapy under image monitoring, schematically presented in a longitudinal section, in accordance with the invention.

FIG. 4 shows the second embodiment of a device for radiation therapy under image monitoring, schematically in plan view.

FIG. 5 shows a third embodiment of a device for radiation therapy under image monitoring, schematically in a longitudinal section, in accordance with the invention.

FIG. 6 shows the third embodiment of a device for radiation therapy under image monitoring, schematically in plan view.

DESCRIPTION OF THE PREFERRED EMBODIMENTS

FIGS. 1 and 2 show (in longitudinal section and in plan view, respectively) a schematic representation of a first embodiment of the invention for radiation therapy under image monitoring that has a magnetic resonance device and an exposure device. Image data of an examination subject U are generated with the magnetic resonance device, and in particular position and dimensions of the examination subject are monitored.

Only one magnet 1 and one gradient system 2 and, schematically, one control unit 8 of the magnetic resonance device are shown. Additional components of the magnetic resonance device such as radio-frequency antennas for radiation of excitation pulses and for acquisition of signals, display and image processing units and their cooperation are well known and therefore need not be shown nor described in detail herein.

The exposure device is also only schematically represented by a radiation source 5 and a control unit 9. A linear accelerator is advantageously used as an exposure device. Alternatively, other radiation sources (for example cobalt sources) can be used. Here as well, the respective radiation generation types and their components are well known and therefore need not be presented nor described in detail therein.

The magnet 1 of the first exemplary embodiment is a cylindrical magnet 1 with an inner cavity 11 in which the gradient system 2 is arranged.

The radiation source 5 of the exposure device is arranged outside of the magnet 1 and is fashioned to be static. The radiation source 5 emits a therapy beam 6 (thick dashed line), controlled by the control unit 9.

A patient support 3 on which a patient P, who contains an examination object U, can be borne such that the examination object U is located in the beam path of the therapy beam 6 can be introduced into the cavity 11, controlled by a control unit 10.

In order to be able to minimize a radiation dose (applied by the therapy beam 6) outside of the examination subject to be exposed and to protect healthy tissue, the patient support 3 can be rotated on a rotation axis A. The radiation dose thereby concentrates in the region of the rotation axis A.

The magnet 1 is thereby advantageously arranged vertically so that the patient P can be raised or, respectively, lowered from above or below into the cavity 11 of the magnet in a standing or sitting position by means of the patient support 3, for example by means of hydraulic or pneumatic lifting and lowering devices or by means of a suspension enabling a lowering into the magnet. In this arrangement the rotation axis A is vertical.

However, it is also conceivable to arrange the magnet 1 in a conventional, horizontal manner and to bear the patient P in a horizontal position on the patient support 3 that can be moved into the cavity 11 of the magnet 1 in a conventional way. Depending on the embodiment, fixing components 4a, 4b attached to the patient support 3 are adapted as necessary. The rotation axis A would thereby be horizontal.

The fixing components 4a, 4b enable a defined rotation movement of the patient P and therefore of the examination object U in that they prevent unintentional movements of the patient P. At the same time, the fixing components 4a, 4b ensure that during the exposure the patient P need exert no force in order to hold a specific position. For example, the fixing components 4a, 4b can be executed in the form of parts 4a supporting the patient P (for instance backrests, posts or seat surfaces) or in the form of restrictive elements 4b (for example belts or bands). The fixing components 4a, 4b are advantageously anatomically molded.

In the first exemplary embodiment, the therapy beam 6 penetrates the magnet 1 from the outside, passes through the gradient system 2 into the inner cavity of the magnet 1, and there strikes an examination object U to be treated via therapy. For this the magnet 1 (and if necessary the gradient system 2) comprises a radiation-permeable area 7 or 7', that the therapy beam 6 can penetrate unhindered. No materials that can scatter or attenuate the therapy beam 6 are present in the radiation-permeable areas 7 and 7'.

In a simple embodiment, the radiation-permeable areas 7 and 7' are free of material. In simplified term, they represent a "hole" through the magnet 1 and the gradient system 2.

Alternatively, parts that are located in a radiation-permeable area 7, 7' are produced from corresponding radiation-permeable material (for example from plastics, for instance polyethylene, polyethylene terephthalate (PET) and/or polyamide that can possibly also be glass fiber-reinforced), and/or individual components (in particular conductive components such as coils) of the magnet 1 and/or of the gradient system 2 are arranged in a manner so that the radiation-permeable areas 7 and 7' are free of materials scattering or attenuating the therapy beam 6.

A gradient system particularly suitable for this, known as a "multi-segment system" with local magnetic field gradients, is disclosed in DE 10 2005 051 021 A1, for example. By dividing the gradient system into segments, these can be flexibly arranged so that the radiation attenuation by the coils of the gradient system can be reduced in specific areas.

FIGS. 3 and 4 show (again in longitudinal section and in plan view, respectively) a schematic representation of a second embodiment of a device for radiation therapy under image monitoring, which second embodiment comprises a magnetic resonance device and an exposure device. Image data of an examination subject U are generated with the magnetic resonance device, and in particular position and dimensions of the examination subject are monitored.

Again, only one magnet 1' and one gradient system 2' and schematically one control unit 8 of the magnetic resonance device are shown. Additional components of the magnetic resonance device, for example radio-frequency antennas for radiation of excitation pulses and for acquisition of signals, display and image processing units as well as their cooperation, are well known and therefore need not be shown nor described in detail herein.

The exposure device is again also only schematically represented by a radiation source 5' and a control unit 9. A linear accelerator is advantageously used as an exposure device. Alternatively, other radiation sources (for example cobalt sources) can be used. Here as well, the respective radiation generation types and their components are well known and therefore need not be shown nor described in detail herein.

In the second exemplary embodiment, the magnet 1' is a cylindrical magnet 1 with an inner cavity 11' in which the gradient system 2' is arranged and into which a patient support 3 in addition to the patient P can be introduced, controlled by a control unit 10.

The gradient system 2' is asymmetrically arranged in order to achieve space for the radiation source 5' within the cavity 11'. For example, electrons are thereby accelerated in the radiation source and deflected at the level of a radiation-permeable area 7" (for example by means of an electromagnet) and directed at a target anode (not shown) to generate the therapy beam 6'. The electromagnet is fashioned from non-ferromagnetic materials in order to prevent unwanted interactions with the surrounding magnetic fields. Since it must operate in a strong, external magnetic field, it is correspondingly modified relative to conventional beam-deflecting electromagnets.

Although the radiation source 5' is arranged inside the magnet 1', this needs to be fashioned only slightly larger than in the first exemplary embodiment (since the radiation source 5' is fashioned to be static) in order to offer sufficient space for the radiation source 5', the gradient system 2' and the patient support 3 in addition to the patient P.

Controlled by the control unit 9, the radiation source 5' radiates a therapy beam 6' (thick dashed line). The patient support 3 bears a patient P, who contains an examination object U, such that the examination object U is located in the beam path of a therapy beam 6' radiated by said radiation source 5'.

As in the first exemplary embodiment, the patient support 3 can be rotated on a rotation axis A in order to minimize the radiation dose applied by the therapy beam 6' outside of the examination subject to be exposed and to protect surrounding healthy tissue.

The magnet 1' can again be arranged vertically or horizontally. The patient support 3 and possible fixing means 4a, 4b comprised by it are to be correspondingly adapted. In order to avoid repetition, the specification of FIGS. 1 and 2 is referenced.

In this second embodiment, the therapy beam 6' does not need to penetrate through the magnet 1', rather only through the gradient system 2'. For this purpose, the gradient system 2' has a radiation-permeable area 7". The statements on the specification of FIGS. 1 and 2 is likewise referenced with regard to design possibilities of this radiation-permeable area 7".

FIGS. 5 and 6 show (again in a longitudinal section or in plan view) a schematic representation of a third embodiment of a device for radiation therapy under image monitoring, which third embodiment comprises a magnetic resonance device and an exposure device. Image data of an examination object U are generated with the magnetic resonance device, and in particular position and dimensions of the examination subject are monitored.

Again, only one magnet 1" and one control unit 8 are of the magnetic resonance device schematically shown. Additional components of the magnetic resonance device—for example a gradient system, radio-frequency antennas for radiation of excitation pulses and for acquisition of signals, display and image processing units as well as their cooperation—are fashioned in a typical manner and therefore need not be shown nor described in detail herein.

The exposure device is again also only schematically represented by a radiation source 5" and a control unit 9. The same radiation sources as in the preceding embodiments are used.

The U-shaped, open magnet 1" in this exemplary embodiment comprises a yoke 12 and two pole shoes 13a and 13b, A free space into which a patient support 3 in addition to the patient P can be introduced, controlled by a control unit 10, is between the pole shoes 13a and 13b.

The radiation source 5" is arranged on the side of the magnet 1" opposite the yoke 12 and can, controlled by the control unit 9, radiate a therapy beam 6" (thick dashed line) at the patient P without hindrances in the beam path.

As in the preceding exemplary embodiments, the patient support bears a patient P who possesses an examination subject U, such that the examination subject is located in the beam path of a therapy beam 6" radiated by the radiation source 5".

Furthermore, as in the preceding exemplary embodiments, the patient support 3 can be rotated on a rotation axis A in order to minimize the radiation dose applied by the therapy beam 6" outside of the examination subject to be exposed and to protect surrounding healthy tissue.

The magnet 1" can again be arranged vertically or horizontally (as is conventional). The patient support 3 and possible fixing means 4a, 4b comprised by it are to be correspondingly adapted. The specification of FIGS. 1 and 2 is again referenced for this.

All exemplary embodiments enable a therapeutic exposure of an examination subject of a patient under image monitoring by the magnetic resonance device. An isocenter of the exposure is thereby located in an examination volume of the magnetic resonance device.

The image monitoring by means of the magnetic resonance device results by means of fast acquisition sequences, for example, that allow a real-time imaging with acquisition speeds of under one second per image and/or with the aid of post-processing programs that, for example, compensate for the known rotation movement. It is likewise conceivable that the rotation movement ensues in specific angle steps (for example every few degrees) and the image monitoring ensues at the idle times between the steps. The use of older, insufficiently quick magnetic resonance devices is also possible in this way.

For example, a cross-sectional area of the therapy beam 6, 6', 6" is thereby adapted in a prevalent manner (for example via a multi-leaf collimator (MLC)) to the exposed cross-section of the examination object U. The position of the patient support 3 is also adapted as necessary during an exposure. The control units 8, 9, 10 (which can also be fashioned as a single control unit) obtain the data required for this via the image monitoring by means of the magnetic resonance device.

A sufficient rotation speed of the patient support 3 is derived from the requirement to be able to rotate the patient around his body axis approximately once per exposure session to realize an exposure therapy (for example with an IMRT method; IMRT—intensity-modulated radiotherapy). Typical rotation speeds might therefore lie approximately on the order of 1 degree per second. The rotation axis thereby does not have to lie parallel to the beam path of the therapy beam 6, 6', 6". Only a partial rotation (<360°) of the examination subject can possibly also be sufficient for an exposure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for radiation therapy with image monitoring, comprising:

a magnetic resonance device configured to generate magnetic resonance images of an examination object of a patient for image monitoring of the examination object of the patient located in an examination volume of the magnetic resonance device;

a statically-mounted exposure device, comprising a hardware component, that exposes the examination object in the examination volume to therapeutic beams emitted from said hardware component;

a patient support configured to vertically support the patient in an upright position and configured to cause the examination object to be rotated, relative to the magnetic resonance device and to the exposure device, with said patient in said upright position around a vertically proceeding rotation axis;

said magnetic resonance device comprising a magnet, which participates in generation of said magnetic resonance images by generating a static magnetic field, said magnet being configured to surround or enclose at least a portion of said hardware component of said exposure device and at least a portion of said examination object with said hardware component in said static magnetic field; and said magnet of said magnetic resonance device comprising a bore in which said examination volume is located, and said hardware component being located in said bore.

2. A system as claimed in claim 1 wherein the patient support comprises fixing components that are configured to fix the patient to the patient support in said upright position.

3. A system as claimed in claim 1 wherein said magnetic resonance device comprises a gradient system in said bore, and wherein said gradient system comprises a radiation permeable area penetrable by said therapy beam with substantially no attenuation or scattering of said therapy beam, and wherein said hardware component is located between a surface of said bore and said gradient system.

4. A method for administering radiation therapy to an examination object implemented with image monitoring, comprising the steps of:
    exposing an examination object in a patient to therapeutic beams emitted by an exposure device;
    at least during a portion of a time during which said examination object is exposed to said therapeutic beams, acquiring magnetic resonance imaging data from the examination object with a magnetic resonance device having an examination volume in which the examination object is located, and generating a magnetic resonance image of the examination object from the magnetic resonance data using a magnet of said magnetic resonance device that generates a static magnetic field, said magnet comprising a bore in which said examination volume is located;
    locating a hardware component of said exposure device in said bore, and emitting said therapeutic beams from said hardware component of said exposure device into said examination volume of said magnetic resonance device;
    vertically supporting the patient on a patient support in an upright position while acquiring said magnetic resonance data and while exposing the examination object to said therapeutic beams, and rotating the examination object, relative to the magnetic resonance device and the exposure device, with the patient in said upright position on said patient support, around a vertically proceeding rotation axis; and
    orienting said magnet of said magnetic resonance device to surround or enclose at least a portion of said hardware component of said exposure device and at least a portion of said examination object with said hardware component in said static magnetic field.

5. A system for radiation therapy with image monitoring, comprising:
    a magnetic resonance device configured to generate magnetic resonance images of an examination object of a patient for image monitoring of the examination object of the patient located in an examination volume of the magnetic resonance device;
    a statically-mounted exposure device, comprising a hardware component that exposes the examination subject in the examination volume to therapeutic beams emitted from said hardware component;
    a patient support configured to support the patient and configured to cause the examination object to be rotated relative to the magnetic resonance device and to the exposure device around a rotation axis; and
    said magnetic resonance device comprising a magnet, which participates in generation of said magnetic resonance images by generating a static magnetic field, said magnet being configured to surround or enclose at least a portion of said hardware component of said exposure device and at least a portion of said examination object with said hardware component in said static magnetic field; and
    said magnet of said magnetic resonance device comprising a bore in which said examination volume is located, and said hardware component being located in said bore.

6. A system as claimed in claim 5 wherein the patient support comprises fixing components that are configured to fix the patient to the patient support in said upright position.

7. A system as claimed in claim 5 wherein said magnetic resonance device comprises a gradient system in said bore, and wherein said gradient system comprises a radiation permeable area penetrable by said therapy beam with substantially no attenuation or scattering of said therapy beam, and wherein said hardware component is located between a surface of said bore and said gradient system.

8. A method for administering radiation therapy to an examination object implemented with image monitoring, comprising the steps of:
    at least during a portion of a time during which said examination object is exposed to said therapeutic beams, acquiring magnetic resonance imaging data from the examination object with a magnetic resonance device having an examination volume in which the examination object is located, and generating a magnetic resonance image of the examination object from the magnetic resonance data using a magnet of said magnetic resonance device that generates a static magnetic field, said magnet comprising a bore in which said examination volume is located;
    locating a hardware component of said exposure device in said bore, and emitting said therapeutic beams from said hardware component of said exposure device into said examination volume of said magnetic resonance device;
    supporting the patient on a patient support while acquiring said magnetic resonance data and while exposing the examination object to said therapeutic beams, and rotating the examination object, relative to the magnetic resonance device and the exposure device, on the patient support around a rotation axis; and
    orienting said magnet of said magnetic resonance device to surround or enclose at least a portion of said hardware component of said exposure device and at least a portion of said examination object with said hardware component in said static magnetic field.

9. A system as claimed in claim 1 wherein said patient has a caudal-cranial axis, and wherein said hardware component is located substantially parallel to said caudal-cranial axis.

10. A method as claimed in claim 4 wherein said patient has a caudal-cranial axis, and comprising orienting said hardware component so as to be substantially parallel to said caudal-cranial axis.

11. A system as claimed in claim 5 wherein said patient has a caudal-cranial axis, and wherein said hardware component is located substantially parallel to said caudal-cranial axis.

12. A method as claimed in claim 8 wherein said patient has a caudal-cranial axis, and comprising orienting said hardware component so as to be substantially parallel to said caudal-cranial axis.

* * * * *